(12) United States Patent
Niznick

(10) Patent No.: US 7,677,891 B2
(45) Date of Patent: Mar. 16, 2010

(54) TAPERED ENDOSSEOUS DENTAL IMPLANTS WITH EXTERNAL MULTIPLE LEAD THREADS

(75) Inventor: Gerald A. Niznick, Las Vegas, NV (US)

(73) Assignee: Implant Direct Int'l, Inc., Las Vegas, NV (US)

( * ) Notice: Subject to any disclaimer, the term of this patent is extended or adjusted under 35 U.S.C. 154(b) by 0 days.

(21) Appl. No.: 11/047,959

(22) Filed: Feb. 1, 2005

(65) Prior Publication Data

US 2006/0172258 A1    Aug. 3, 2006

(51) Int. Cl.
*A61C 8/00* (2006.01)
(52) U.S. Cl. ...................................... 433/174
(58) Field of Classification Search .............. 433/173, 433/174, 221, 225; 606/73
See application file for complete search history.

(56) References Cited

U.S. PATENT DOCUMENTS

| 4,960,381 | A | | 10/1990 | Niznick |
| 5,259,398 | A | | 11/1993 | Vrespa |
| 5,588,838 | A | * | 12/1996 | Hansson et al. ............. 433/173 |
| 5,593,410 | A | | 1/1997 | Vrespa |
| RE37,646 | E | | 4/2002 | Zuest |
| 6,547,564 | B1 | * | 4/2003 | Hansson ..................... 433/174 |
| 6,896,517 | B1 | * | 5/2005 | Bjorn et al. ................. 433/174 |
| 2004/0006346 | A1 | * | 1/2004 | Holmen et al. ............... 606/73 |
| 2005/0287496 | A1 | * | 12/2005 | Niznick ..................... 433/173 |

* cited by examiner

*Primary Examiner*—Ralph A Lewis
(74) *Attorney, Agent, or Firm*—Patrick F. Bright

(57) ABSTRACT

Endosseous dental implants tapered over at least part of their length, include two separate portions, a shorter proximal region with half the distance and half the depth between adjacent peaks of multiple lead threads as the longer distal region which has half the number of multiple lead threads as in the proximal region.

17 Claims, 1 Drawing Sheet

TAPERED ENDOSSEOUS DENTAL IMPLANTS WITH EXTERNAL MULTIPLE LEAD THREADS

This invention relates to tapered endosseous dental implants with external multiple lead threads on the tapered body of the implants. These implants may be one piece or two-piece, and may include an internal passage with internal threads, and one or more wrench-engaging surfaces. These implants may also include a lead-in bevel or chamfer at or near the opening to the internal passage. This bevel or chamfer may be inside the internal passage or outside, at or near the opening into the passage.

These endosseous implants comprise an elongated, externally-threaded body, tapered over at least part of its length, and, optionally, an external, distal, self-tapping feature. The proximal end of these implants may comprise an unthreaded cylindrical portion, proximal to the externally-threaded portion of the body, and an inwardly-tapering, proximally-extending, unthreaded proximal portion. This proximal portion may include a flat or tapered upper surface with an opening to an internal passage that may include one or more wrench-engaging surfaces and one or more threaded regions.

The external threads on the body of these implants include a distal region with multiple lead threads, e.g., triple or double lead threads. These threads may be, for example, V-shaped, buttress-shaped, square-shaped, or some other shape. A proximal region of the threaded external body also comprises multiple lead threads, with twice the number of leads as the distal region, e.g., quadruple lead threads in the proximal region, with double lead threads in the distal region, or six lead threads in the proximal region, with triple lead threads in the distal region, where each thread may have the same pitch. Preferably, all threads have substantially the same pitch, with the distance between adjacent threads in the proximal region preferably about half the distance between adjacent threads in the distal region. The linear length of the proximal region is preferably not more than about one-third the linear length of the body. The linear length of the distal region with double lead threads is preferably not more than about two-thirds the linear length of the body.

As an example, with V-shaped threads, the pitch of the threads may be, for example, 1.2 mm, with the distance between adjacent quadruple lead threads about 0.3 mm in the proximal region, and about 0.6 mm between double lead threads in the distal region. With buttress/flat-based threads, the threads may have a pitch of about 1.6 mm with the distance between adjacent quadruple lead threads about 0.4 mm in the proximal region, and about 0.8 mm between double lead threads in the distal region. In such embodiments, the threads in the proximal region may start every 90°, and every 180° in the distal region.

The body of the implant may taper distally over more than 50% of its linear length, and over at least about 30% of the linear length of the body in some embodiments, and over at least about 50% of the linear length of the body in some embodiments, such that the crest of substantially all the peaks in the distal region are not on an axial plane parallel to the longitudinal axis of the implant. For example, the proximal externally-threaded body region may be untapered, and comprise up to about 65% of the linear length of the body, but the distal, externally-threaded region of the implant body may taper about 35% of the linear length of the body.

In some embodiments, e.g., tapered implants with double lead threads in the distal region and quadruple lead threads in the proximal region, the trough/valleys between adjacent peaks of the threads are at least about 0.2 mm in depth. Some embodiments may include, at the proximal end of the body of the implant, an unthreaded portion that comprises more than about 4%, preferably more than about 4.5%, and up to 15% of the linear length of the implant.

As these implants are threaded or screwed into an opening in the jawbone of a patient, the multiple lead threads on the distal surface of the implant body enter and cut threads in the opening. When the multiple lead threads on the proximal region of the implant body enter this opening, the implant can continue to be threaded, without cross threading, into threads already formed inside the opening.

For example, where the distal region of the implant body includes double lead threads, two of the quadruple lead threads follow the threads created and formed in bone by the double lead threads. The other two threads in the proximal region that are located between the two threads that follow the double lead proximal threads, either cut their way into the bone between the threads, or bypass the existing threads, but do not cut across threads formed in the bone cavity by the double lead threads.

As an additional example, with triple lead threads at the distal region, and six threads starting every 60° in the proximal region, three of the triple lead threads in the six-thread region follow the threads created in bone by the triple lead threads, and the other three threads cut their way into the bone between the threads formed by the triple lead thread region, or are positioned without disturbing the threads already formed.

These implants may also include one or more of the features of the endosseous dental implants, abutments and other related products, disclosed in the following U.S. patent applications:

Externally-Threaded Endosseous Dental Implants With Internal Abutment Engaging And Fixture Mount Engaging Surfaces (D9471);

One-Piece, Screw-Receiving, Externally-Threaded Endosseous Dental Implants And Related Transfer Components, Comfort Caps And Abutments (D9470);

U.S. Pat. Ser. No. 10/877460, filed Jun. 25, 2004, entitled "Endosseous Dental Implant" P9462);

U.S. Pat. Ser. No. 10/883,275, filed Jul. 01, 2004, entitled "Endosseous One-Piece Screw-Type Dental Implants" P9456);

U.S. Pat. Ser. No. 10/741023, filed Dec. 19, 2003, entitled "Multi-part Abutment And Transfer Cap For Use With An Endosseous Dental Implant With Non-Circular, Beveled Implant Abutment Interface" (D9452);

U.S. Pat. Ser. No. 10/741,061, filed Dec. 19, 2003, entitled "Endosseous Dental Implant" (D9443); and U.S. Pat. No. 4,960,381, issued Oct. 2, 1990, entitled "Screw-Type Dental Implant Anchor"

BRIEF DESCRIPTION OF THE DRAWINGS

These tapered endosseous dental implants with external multiple lead threads can better be understood by reference to the drawings in which.

DETAILED DESCRIPTION OF THE DRAWINGS

Figure 1:
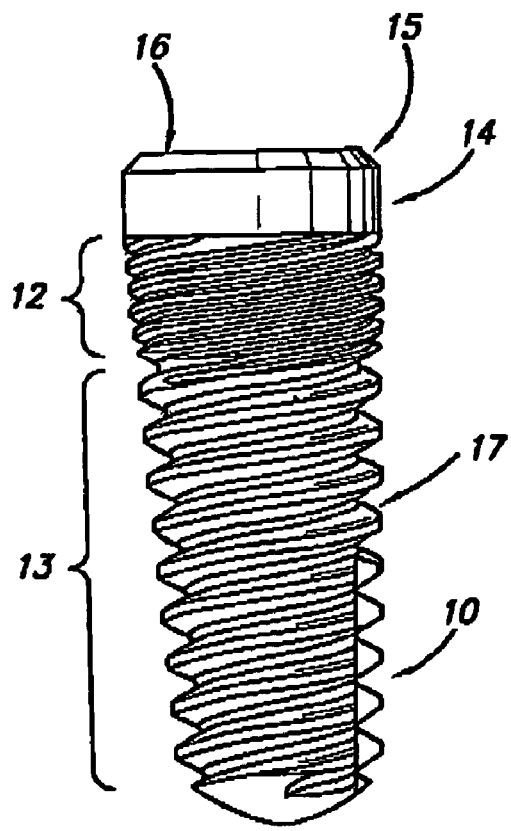
FIG. 1 shows a side elevation view of a tapered endosseous dental implant with a tapered, externally-threaded body that includes a distal region with V-shaped double lead threads and a proximal region with V-shaped quadruple lead threads.

FIG. 1 shows a tapered endosseous dental implant 10 in side elevation view. Implant 10 includes tapered body 11. Body 11 includes two externally-threaded regions 12 and 13. Proximal, externally-threaded region 12 includes V-shaped quadruple lead threads, all of which have the same pitch. Distal portion 13 includes V-shaped double lead threads. Spacing between adjacent threads is substantially the same. At the proximal end of dental implant 10, and proximal to threaded portion 12, is unthreaded cylindrical portion 14. Proximal to unthreaded cylindrical portion 14, is proximal unthreaded portion 15, which extends proximally, and tapers inwardly, to flat surface 16 atop dental implant 10. Distal portion 13 comprises about 30% of the linear length of body 11. Body 11 tapers about 50% from the proximal end of portion 13 to its distal end.

Figure 2:
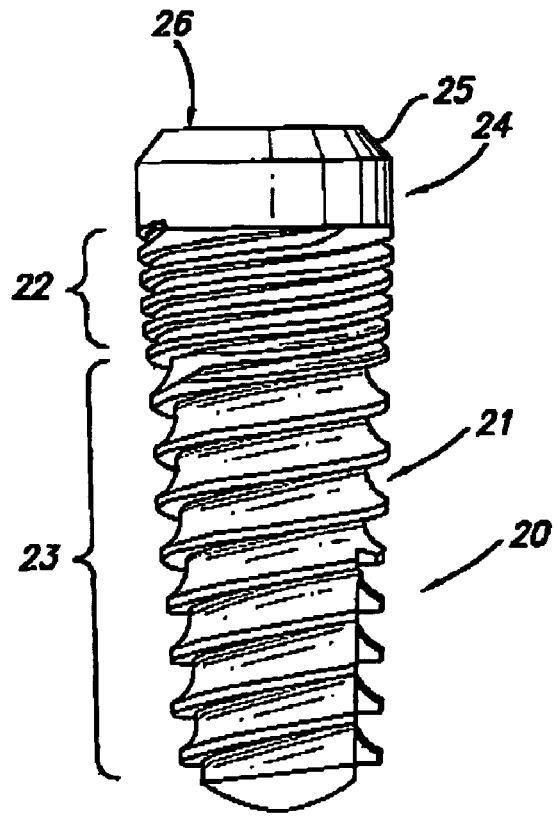
FIG. 2 shows a side elevation view of a tapered endosseous dental implant with a tapered, externally-threaded body that includes a distal region with flat or buttress-shaped double lead threads and a proximal region with flat or buttress-shaped quadruple lead threads.

FIG. 2 is a tapered endosseous dental implant 20 in side elevation view. Implant 20 includes tapered body 21. Body 21 includes two externally-threaded regions 22 and 23. Proximal, externally-threaded region 22 includes buttress-shaped or flat-profile quadruple lead threads, all of which have the same pitch. Distal portion 23 includes double lead flat profile or buttress-shaped threads. Spacing between adjacent threads is substantially the same. At the proximal end of dental implant 20, and proximal to threaded portion 22, is unthreaded cylindrical portion 24. Proximal to unthreaded cylindrical portion 24, is proximal unthreaded portion 25, which extends proximally and tapers inwardly to flat surface 26 atop dental implant 10. Distal portion 23 comprises about 30% of the linear length of body 21. Body 21 tapers about 50% from the proximal end of portion 23 to its distal end.

The invention claimed is:

1. An endosseous dental implant, comprising an elongated, externally-threaded body, tapered over at least part of its length, that comprises at least two external regions of multiple lead threads, including a distal region comprising double lead threads, and a proximal region comprising quadruple lead threads, wherein all of said threads have substantially the same pitch, and wherein the distance between adjacent thread peaks in said proximal region is about half the distance between adjacent thread peaks in said distal region, whereby the threads on said proximal region fit into threads formed in the jawbone of a patient by the threads on said distal region upon insertion of said implant into said jawbone, or cut into bone between said jawbone threads without cutting across said jawbone threads.

2. The dental implant of claim 1, wherein said proximal region is shorter than said distal region.

3. The dental implant of claim 2, wherein said proximal region is less than half the linear length of the distal region.

4. The dental implant of claim 1 or claim 2, further comprising an internal passage in the body of said implant, said passage having an opening at the top of said implant, said passage including internal threads, internal wrench-engaging surfaces or both, said passage terminating inside said dental implant.

5. An endosseous dental implant, comprising an elongated, externally-threaded body, tapered over at least part of its length, that comprises at least two external regions of multiple lead threads, including a distal region comprising triple-lead threads, and a proximal region comprising six-lead threads, wherein all of said threads have substantially the same pitch, and wherein the distance between adjacent thread peaks in said proximal region is about half the distance between adjacent thread peaks in said distal region, whereby the threads on said proximal region fit into threads formed in the jawbone of a patient by the threads on said distal region upon insertion of said implant into said jawbone, or cut into bone between said jawbone threads without cutting across said jawbone threads.

6. The dental implant of claim 5, wherein said proximal region is shorter than said distal region.

7. The dental implant of claim 5, wherein said proximal region is less than half the linear length of the distal region.

8. The dental implant of claim 5 or claim 6 or claim 7, further comprising an internal passage in the body of said implant, said passage having an opening at the top of said implant, said passage including internal threads, internal wrench-engaging surfaces or both, said passage terminating inside said dental implant.

9. The dental implant of claim 1 or claim 2 or claim 3 or claim 5 or claim 6 or claim 7, wherein said body tapers over at least about 35% of its linear length.

10. The dental implant of claim 1 or claim 2 or claim 3 or claim 5 or claim 6 or claim 7, wherein the troughs between adjacent peaks of the threads are at least about 0.2 mm in depth.

11. The dental implant of claim 1 or claim 2 or claim 3 or claim 5 or claim 6 or claim 7, wherein said body includes an unthreaded portion proximal to the threaded regions on the externally-threaded regions comprising more than about 4% of the linear length of said body.

12. An endosseous dental implant, comprising an internal passage in the body of said implant, said passage having an opening at the top of said implant, said passage including internal threads, internal wrench-engaging surfaces or both, said passage terminating inside said dental implant, and an elongated, externally-threaded body that comprises at least two external regions of multiple lead threads, including a distal region comprising double lead threads, and a proximal region comprising quadruple lead threads, wherein all of said threads have substantially the same pitch, and wherein the distance between adjacent thread peaks in said proximal region is about half the distance between adjacent thread peaks in said distal region, whereby the threads on said proximal region fit into threads formed in the jawbone of a patient by the threads on said distal region upon insertion of said implant into said jawbone, or cut into bone between said jawbone threads without cutting across said jawbone threads.

13. The dental implant of claim 12, wherein said proximal region is shorter than said distal region.

14. The dental implant of claim 13, wherein said proximal region is less than half the linear length of the distal region.

15. An endosseous dental implant, comprising an internal passage in the body of said implant, said passage having an opening at the top of said implant, said passage including internal threads, internal wrench-engaging surfaces or both, said passage terminating inside said dental implant, and an elongated, externally-threaded body that comprises at least two external regions of multiple lead threads, including a distal region comprising triple-lead threads, and a proximal region comprising six-lead threads, wherein all of said threads have substantially the same pitch, and wherein the distance between adjacent thread peaks in said proximal region is about half the distance between adjacent threads in said distal region, whereby the threads on said proximal region fit into threads formed in the jawbone of a patient by the threads on said distal region upon insertion of said implant into said jawbone, or cut into bone between said jawbone threads without cutting across said jawbone threads.

16. The dental implant of claim 15, wherein said proximal region is shorter than said distal region.

17. The dental implant of claim 15, wherein said proximal region is less than half the linear length of the distal region.

* * * * *